US010058626B2

(12) United States Patent
Itarashiki et al.

(10) Patent No.: US 10,058,626 B2
(45) Date of Patent: Aug. 28, 2018

(54) STERILIZATION DEVICE AND STERILIZATION METHOD USING SAME

(71) Applicant: SARAYA CO., LTD., Osaka-shi (JP)

(72) Inventors: Tomomasa Itarashiki, Osaka (JP); Norio Onitsuka, Osaka (JP)

(73) Assignee: SARAYA CO., LTD., Osaka-shi, Osaka (JP)

( * ) Notice: Subject to any disclaimer, the term of this patent is extended or adjusted under 35 U.S.C. 154(b) by 255 days.

(21) Appl. No.: 14/404,215

(22) PCT Filed: May 22, 2013

(86) PCT No.: PCT/JP2013/064188
§ 371 (c)(1),
(2) Date: Nov. 26, 2014

(87) PCT Pub. No.: WO2013/179964
PCT Pub. Date: Dec. 5, 2013

(65) Prior Publication Data
US 2015/0209461 A1 Jul. 30, 2015

(30) Foreign Application Priority Data

May 28, 2012 (JP) .................. 2012-120714

(51) Int. Cl.
A61L 2/18 (2006.01)
H05H 1/24 (2006.01)
(Continued)

(52) U.S. Cl.
CPC .................. A61L 2/186 (2013.01); A61L 2/14 (2013.01); A61L 2/18 (2013.01); B01J 19/088 (2013.01); H05H 1/24 (2013.01); A61L 2202/24 (2013.01)

(58) Field of Classification Search
CPC .... A61L 2/186; A61L 2/14; A61L 2/18; B01J 19/088; H05H 1/24
See application file for complete search history.

(56) References Cited

U.S. PATENT DOCUMENTS 5,084,239 A * 1/1992 Moulton ................. A61L 2/20
250/455.11
5,244,629 A 9/1993 Caputo et al.
(Continued)

FOREIGN PATENT DOCUMENTS

CN 1612755 A 5/2005
EP 0 474 137 A2 3/1992
(Continued)

OTHER PUBLICATIONS

Extended European Search Report dated Dec. 17, 2015, by the European Patent Office in corresponding European Patent Application No. 13797786.4. (6 pages).
(Continued)

Primary Examiner — Regina M Yoo
(74) Attorney, Agent, or Firm — Buchanan Ingersoll & Rooney PC

(57) ABSTRACT

A sterilization system comprises a reaction container configured to receive a sterilization object and sterilize the object; means for supplying peracetic acid as an sterilization agent into the reaction container, the peracid agent including at least peracetic acid; means for reducing a pressure in the reaction container; means for ventilating the reaction container; and means for generating plasma at a first predetermined portion for receiving the sterilization object in the reaction container and a second predetermined portion of a fluid passage from a neighborhood of the first predetermined portion to an exterior of the container. The pressure reducing means and the plasma generating means are controlled so
(Continued)

that the plasma is maintained at the predetermined portions in a process during which the pressure in the reaction container is reduced.

4 Claims, 7 Drawing Sheets

(51) Int. Cl.
 *A61L 2/14* (2006.01)
 *B01J 19/08* (2006.01)

(56) References Cited

U.S. PATENT DOCUMENTS

| | | | |
|---|---|---|---|
| 5,413,758 A | 5/1995 | Caputo et al. | |
| 5,869,000 A | 2/1999 | DeCato | |
| 6,060,019 A * | 5/2000 | Spencer | A61L 2/14 34/257 |
| 6,365,102 B1 | 4/2002 | Wu et al. | |
| 7,892,486 B2 * | 2/2011 | Mizuno | A61L 2/14 422/33 |
| 2004/0120869 A1 | 6/2004 | Ko | |
| 2008/0093024 A1 * | 4/2008 | Abe | H01J 37/32183 156/345.44 |
| 2008/0260578 A1 * | 10/2008 | Engemann | A23L 3/28 422/400 |
| 2011/0008209 A1 | 1/2011 | Lee | |

FOREIGN PATENT DOCUMENTS

| | | | |
|---|---|---|---|
| EP | 1 040 839 A1 | 10/2000 | |
| EP | 1040839 A1 * | 10/2000 | ............... A61L 2/14 |
| JP | 52-23888 A | 2/1977 | |
| JP | S5367986 A | 6/1978 | |
| JP | 57-3650 A | 1/1982 | |
| JP | 2780228 B2 | 5/1998 | |
| JP | 2000-308675 A | 11/2000 | |
| JP | 2004-357888 A | 12/2004 | |
| JP | 2011-235153 A | 11/2011 | |
| WO | 2009/005252 A2 | 1/2009 | |

OTHER PUBLICATIONS

Office Action dated May 20, 2016, by the State Intellectual Property Office of China in corresponding Chinese Patent Application No. 201380027446.7 with a partial English-language translation (11 pages).

Office Action (Official Action [Inquiry] of the Substantive Examination) dated May 31, 2017, by the Russian Patent Office in corresponding Russian Patent Application No. 2014147115 and an English Translation of the Office Action. (13 pages).

International Search Report (PCT/ISA/210) dated Jun. 25, 2013, by the Japanese Patent Office as the International Searching Authority for International Application No. PCT/JP2013/064188.

\* cited by examiner

STERILIZATION DEVICE AND STERILIZATION METHOD USING SAME

TECHNICAL FIELD

The present invention relates to a sterilization device and a sterilization method using the sterilization device. In particular, the present invention relates to a sterilization device which performs a sterilization process using peracid agent as sterilization agent, including at least peracetic acid, and a sterilization method using the sterilization device.

BACKGROUND OF THE INVENTION

Conventionally, there have been used various methods for sterilizing medical devices, which perform a sterilization process at an elevated temperature, such as a dry-heat sterilization process and a high-pressure steam sterilization process. Recently, some medical devices have been put to practical use, in which at least a part thereof is made of material with low heat resistance according to a diversification of the devices and those devices need to be sterilized at a lower temperature. Also, for devices with elongate hollow tubes such as endoscopic instruments, the interiors of the elongate hollow tube thereof should be sterilized.

To meet the requirements, there have been known a sterilization method in which a sterilization object is received within a reaction container, vacuum is introduced in the reaction container, and then the sterilization agent is injected into the vacuum, causing vaporization and expansion of the injected agent and then allowing the vaporized agent to enter the interior of the elongate hollow tube, which sterilizes the interior of the tube in its entirety in a low temperature environment.

In this sterilization method, hydrogen peroxide is typically used as sterilization agent. However, the hydrogen peroxide by itself may not be satisfied for the sterilization of the medical devices which always need an advanced sterilization. To counter this problem, there has been known a method which uses peracid agent including at least peracetic acid, as a sterilization agent, which is capable of exerting an advanced sterilization effect even with a relatively small amount thereof.

For example, patent documents 1 and 2 disclose a sterilization method which is designed to obtain an advanced sterilization effect by applying plasma in the sterilization process in which the agent is vaporized in the vacuum as described above.

PRIOR ART DOCUMENT(S)

Patent document 1: JP 2780228 B
Patent document 2: JP 4526649 B

SUMMARY OF THE INVENTION

As described above, the use of peracid agent including at least peracetic acid as sterilization agent, even with a relatively small amount thereof, attains an increased sterilization effect. As is known, however, the peracetic acid usually exists in the form of equilibrium mixture of pure peracetic acid and other components including acetic acid, hydrogen peroxide, and water and therefore has a very irrigating odor, which needs to implement a counter measure for minimizing an adverse affect on the working environment which might be caused by the irrigating odor generated during the sterilization process. Practically, the adverse affect due to the irrigating odor is needed to be reduced with a relatively simple mechanism, without any need of incorporating a large, costly deodorization equipment, for example.

Taking the above in consideration, a major purpose of the invention is to deodorize the remaining agent after sterilization by means of a relatively simple mechanism in the sterilization process which uses peracid agent including at least peraceic acid.

In the course of working in the research and development for this purpose, the inventors of this invention discovered that the peracid agent including peracetic acid was resolved by an application of plasma to the agent after sterilization and, in particular, that the remaining agent in the container after sterilization was effectively deodorized by maintaining the generation of plasma during the pressure reduction process in the passages which extend from the sterilization container to the atmosphere of the sterilization system.

Therefore, the sterilization device of the invention is featured in that it comprises
(a) a reaction container configured to receive a sterilization object and sterilize the object;
(b) means for supplying peracetic acid as an sterilization agent into the reaction container, the peracid agent including at least peracetic acid;
(c) means for reducing a pressure in the reaction container;
(d) means for ventilating the reaction container;
(e) means for generating plasma at a first predetermined portion for receiving the sterilization object in the reaction container and a second predetermined portion of a fluid passage from a neighborhood of the first predetermined portion to an exterior of the container; and
(f) means for controlling the pressure reducing means and the plasma generating means so that the plasma is maintained at the predetermined portions in a process during which the pressure in the reaction container is reduced.

In this invention, the device may comprises a second supplying means for supplying a decomposer or water for accelerating a decomposition of the peracid agent into the reaction container after the sterilization agent has been supplied into the reaction container.

In the invention, the second predetermined portion may be provided either inside or outside or both the reaction container.

A sterilization method of the invention comprises
receiving a sterilization object at a first predetermined portion in a sterilization reaction container;
reducing a pressure in the reaction container and supplying peracetic acid as an sterilization agent into the reaction container, the peracid agent including at least peracetic;
after sterilizing the object, generating plasma at the first predetermined portion and a second predetermined portion of a fluid passage from a neighborhood of the first predetermined portion to an exterior of the container; and
reducing the pressure in the reaction container while maintaining the plasma at the predetermined portions and then ventilating the reaction container.

The method may further comprises supplying a decomposer or water for accelerating a decomposition of the peracid agent into the reaction container after the sterilization agent has been supplied into the reaction container.

According to the invention, in the process of reducing the pressure in the reaction container after the sterilization process using peracetic agent including at least peracid agent, the plasma generation is maintained at the first predetermined portion in the reaction container for receiving the sterilization object and the second predetermined portion of the fluid passage from the neighborhood of the first predetermined portion to the exterior of the system, effectively deodorizing the remaining agent within the container after the sterilization process, which advantageously minimizes adverse affect on the working environment which might cause due to the irritating odor of the agent. Also, the adverse affect due to the irritating odor of the agent is reduced with a relatively simple structure in which, for example, the plasma generation portions and the pressure reduction timings are modified, without any need to install additional large and expensive deodorization equipment.

BRIEF DESCRIPTIONS OF THE DRAWINGS

PREFERRED EMBODIMENTS OF THE INVENTION

Referring to the accompanying drawings, several embodiments of the invention will be described in detail below. In the followings, directional terminologies, such as "upper", "lower", "left", "right", "front", "rear", others combined with such terminology, "clockwise" or "counterclockwise" is used for the better understanding of the invention with reference to the drawings, however; the present invention should not be restrictively interpreted by the meaning of such terminologies.

Figure 1:
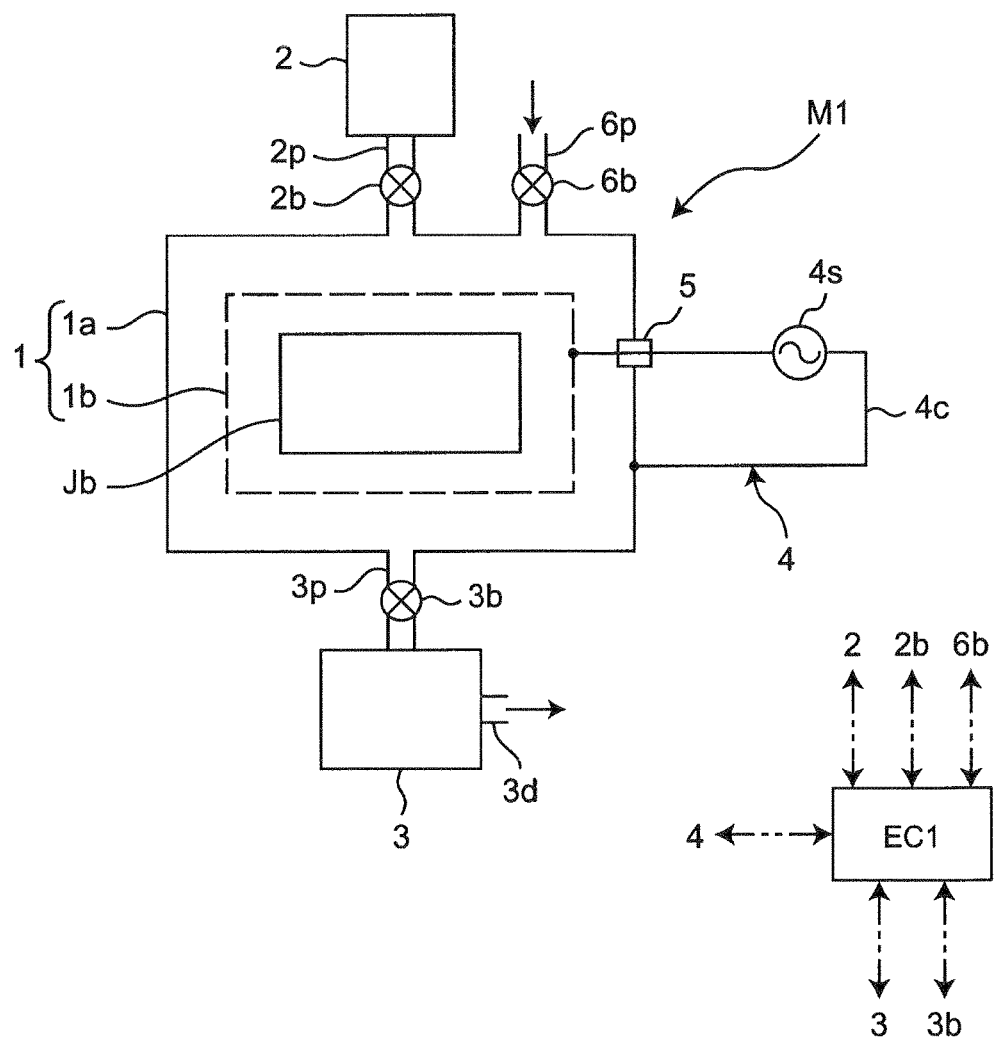
FIG. 1 is a diagram schematically showing a general construction of a sterilization system according to a first embodiment of the invention.

FIG. 1 shows a general construction of a sterilization system according to a first embodiment of the invention. As shown in the drawing, the sterilization system (M1) according to the embodiment has a reaction container (1) for receiving a sterilization object (Jb) during its sterilization, an agent injection unit (2) for injection of peracid agent including at least peracetic acid, as sterilization agent, into the interior of the reaction container (1), a vacuum pump (3) which constitutes a major part of a pressure reduction means for reducing a pressure in the interior of the reaction container (1) and a ventilation means for ventilating the interior of the reaction container (1), and a high-frequency unit (4) which functions as a plasma generating means for generating plasma at a predetermined object receiving portion in the reaction container (1) for receiving the sterilization object (Jb) and a predetermined fluid-passage portion of a fluid passage from a neighborhood of the object receiving portion to the exterior of the system (M1).

The reaction container (1) comprises an external box (1a) which defines an air-tightly sealable interior thereinside and an internal box (1b) which is positioned within the external box (1a). The external and internal boxes (1a, 1b) are made of electrically conductive material with certain strength, rigidity, and corrosion resistance and electrically disconnected from each other. A metal plate such as iron plate may be used for the external and internal boxes (1a, 1b). The external box (1a) is made by bending and machining a commonly-used metal plate to form the air-tightly sealable interior inside the internal box (1a). The internal box (1b) is made by bending and machining a perforated metal plate with a number of perforations defined thereon, allowing gaseous material such as vaporized medical agent or air, liquid material, or plasma to freely move between the interior and exterior of the internal box (1b).

The sterilization object (Jb) such as endoscope is received within the interior of the perforated internal box (1b). The sterilization object (Jb) may be placed directly on the inner surface of the internal box (1b) or on a dedicated support member (not shown) mounted within the internal box (1b).

The sterilization agent injection unit (2) is connected to one side or an upstream side of the reaction container (1) through an injection pipe (2p) with an on-off control valve (2b) for injecting peracetic acid including at least peracid agent, as sterilization agent, into the reaction container (1).

A vacuum pump (3) is connected to the other side or a downstream side of the reaction container (1) through a connection pipe (3p) with an on-off control valve (3b), which allows that a pressure in the interior of the reaction container (1) to be reduced to a predetermined value by controlling the pressure pump (3). The vacuum pump (3) is connected at its downstream side to an exhaust pipe (3d) for exhausting gas drawn from the interior of the reaction container (1) out of the sterilization system (M1).

An air intake pipe (6p) with an on-off control (6b) is provided beside the agent injection unit (2) and connected to the one side or the upstream side of the reaction container (1), which allows fresh air to be introduced into the reaction container (1) for ventilation thereof by opening the control valve (6b), after the sterilization using the sterilization agent and the subsequent pressure reduction in the reaction container (1). The air intake pipe (6p), the on-off control valve (6b), the connection pipe (3p), the on-off control valve (3b), the vacuum pump (3), and the exhaust pipe (3d) constitute means for ventilation of the reaction container (1) which is performed after the completion of each cycle of sterilization process.

An object receiving portion for receiving the sterilization object (Jb) in the reaction container (1) and a fluid passage portion of the fluid passage ranging from a neighborhood of the object receiving portion to the exterior of the system (M1) include the downstream side zone of the sterilization object (Jb) in the internal box (1b) of the reaction container (1), the downstream side zone of the space between the internal and external boxes (1b, 1a), the on-off control valve (3b), the vacuum pump (3), and the exhaust pipe (3d). The fluid passage portion serves as an exhaust passage for exhausting the gas drawn from the reaction container (1) out of the system (M1).

According to the embodiment, a high-frequency unit (4) is provided, as a plasma generation means, outside the reaction container (1) in order to generate plasma at certain positions of the fluid passage. The high-frequency unit (4) has a high-frequency circuit (4v) and a high-frequency power source (4s) provided in the high-frequency circuit. One end of the high-frequency circuit (4c) is electrically connected to the external box (1a) of the reaction container (1). The other end of the high-frequency circuit (4c) is extended though the external box (1a) via a air-tight sleeve (5) and electrically connected to the internal box (1b) so as to generate a plasma between the space between the external and internal boxes (1a, 1b) by the driving of the high-frequency power source (4s).

In order to electrically connect the other end of the high-frequency circuit (4c) to the internal box (1b), the conducting wire of the high-frequency circuit (4c) is needed to be extended through the external box (1a). To this end, the air-tight sleeve (5), which has the same structure and function as the conventional one, is configured so that the conducting wire of the circuit (4c) is sealingly extended through the external box (1a) while maintaining the vacuum within the container (1).

The sterilization system (M1) has a controller (EC1) as a control unit for controlling the entirety of the system. For example, the controller (EC1) has, as a primary part thereof, a microcomputer. The controller (EC1) is mounted on a control panel (not shown) of the sterilization system (M1). The agent injection unit (2), the vacuum pump (3), the high-frequency unit (4), the on-off valves (2b), (3b), and (6b) are connected to the controller for communication therewith so that they are controlled by control signals from the controller (EC1). Each of the on-off valves (2b), (3b), and (6b) may be any one of conventional electro-magnetic valves.

Figure 2:
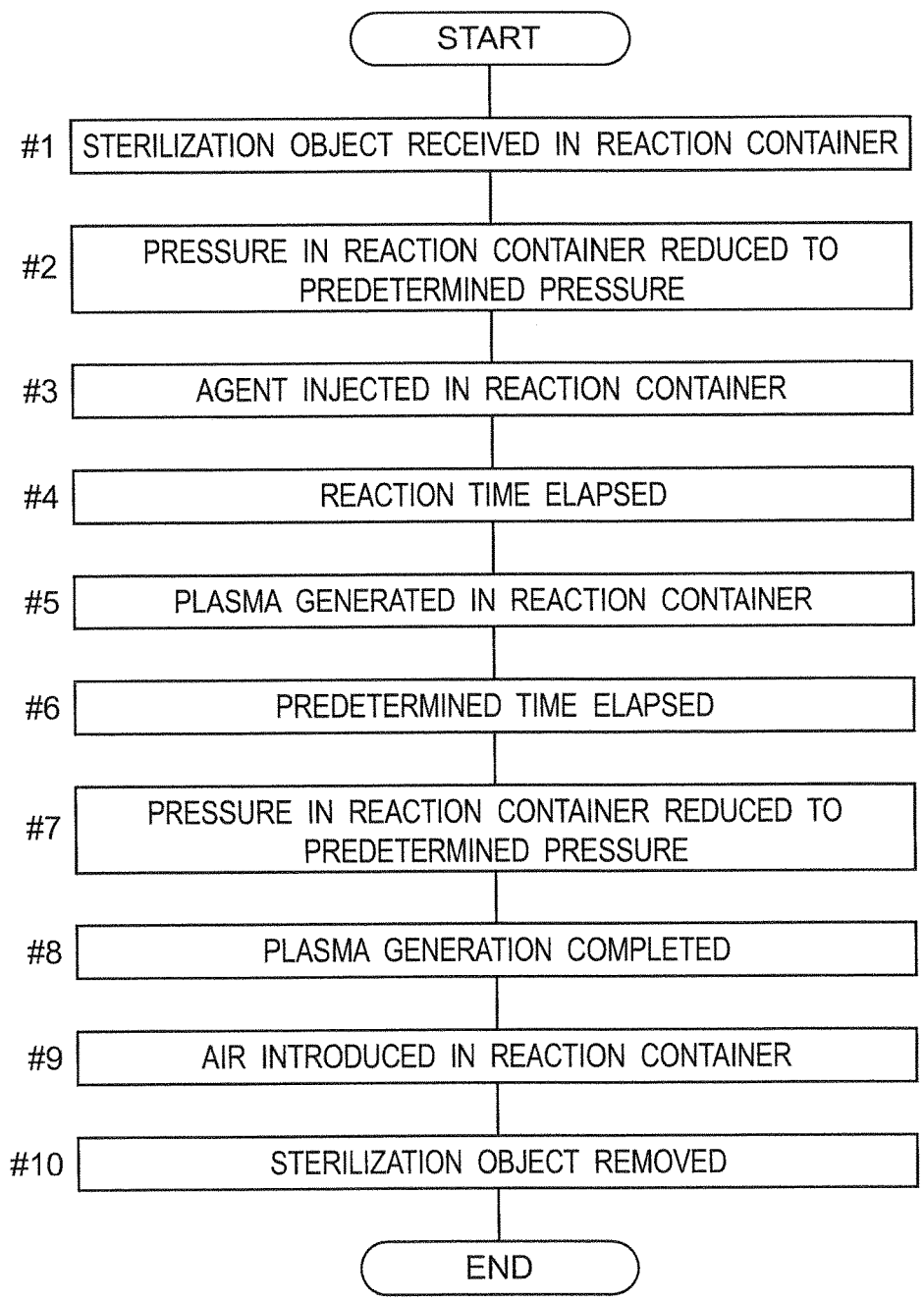
FIG. 2 is a diagram showing a process flow made by the sterilization system according to the first embodiment of the invention.
Figure 3:
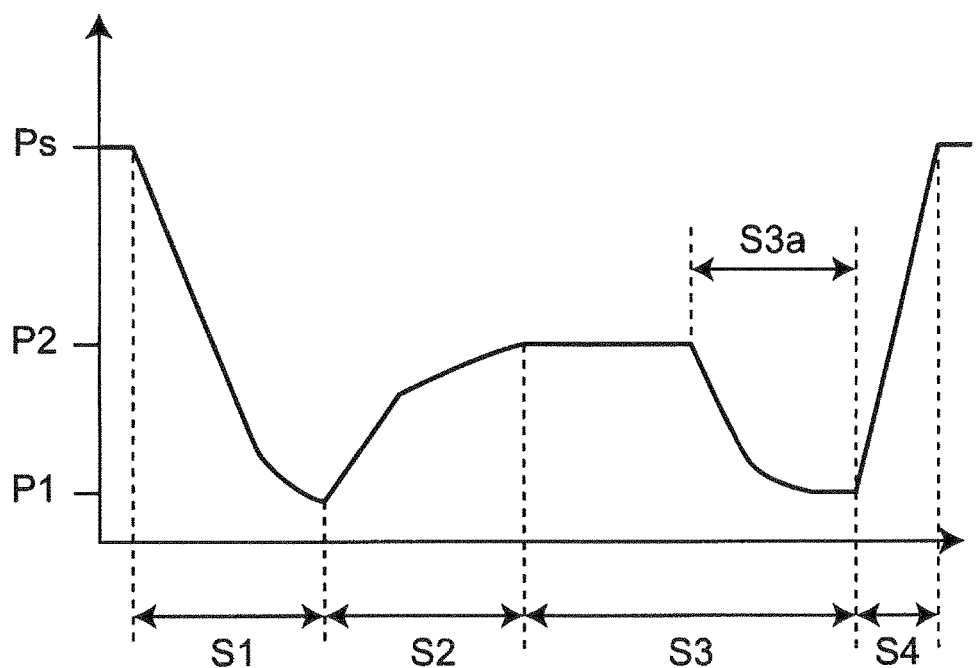
FIG. 3 is a graph showing a pressure variation in a reaction container during the process made by the sterilization system according to the first embodiment.

Next, discussions will be made to a sterilization process of the sterilization system (M1) so constructed. FIG. 2 is a diagram showing a flow of process conducted in the sterilization system (M1). FIG. 3 is a graph showing a pressure variation in the reaction container during the process by the sterilization system (M1).

When the process is initiated, firstly at step #1 the sterilization object (Jb) such as an endoscope is placed on a predetermined portion within the reaction container (1). The predetermined portion is set within the interior of the internal box (1b) as described above. At this moment, the system (M1) is in a de-energized, initial condition in which the valves (2b), (3b), and (6b) are closed. Also, the sterilization object (Jb) is received within the perforated-metal internal box (1b) and the external box (1a) is air-tightly closed.

Next, at step #2 the vacuum pump (3) is driven after the opening of the on-off valve (3b) to reduce the pressure in the interior of the reaction container (1) to a certain pressure (P1) (first pressure reduction process S1 in FIG. 3). When the pressure in the interior of the reaction container is reduced to the certain pressure (P1), at step #3 the on-off valve (3b) is closed and the on-off valve (2b) is opened, allowing the agent injection unit (2) to inject a certain amount of agent into the reaction container (1). As described above, the agent is peracid agent including at least peracetic acid. Details of the agent will be described hereinafter.

When injected into the pressure-reduced reaction container (1), the agent is vaporized immediately, increasing the vapor pressure in the reaction container (1) up to a certain pressure (P2) (Ps>P2>P1). The pressure (P2) is determined by the conditions of the reaction container (1) such as its volume and temperature, and the components and amount of the agent injected in the container (1). In this process, the vaporized agent contacts and sterilizes the entire surface of the object (Jb). In particular, due to the vapor pressure the agent penetrates into the details and depths of the sterilization object (Jb) to sterilize them efficiently. At step #4, the sterilization is maintained for a certain reaction time to enhance the sterilization effect (sterilization process S2 in FIG. 3). The vaporized agent may be injected into the reaction container (1) to improve the diffusion of the agent throughout the reaction container (1).

According to the embodiment, preferably the pressure (P1) is set to be equal or less than 100 Pa in order for the vaporized agent to effectively penetrate into the details and depths of the sterilization object (Jb). The pressure (P2) is determined, according to the amount of injected agent and/or the volume of the reaction container, typically to be 1,000-2,500 Pa.

When the reaction time is elapsed to complete the sterilization process S2, the high-frequency unit (4) is driven at step #5 to initiate a plasma generation process S3 (plasma processing S3 in FIG. 3) in which a plasma is generated within the interior of the reaction container (1), i.e., in the space between the external and internal boxes (1a, 1b). The plasma processing is maintained for a certain time at step #6. When the time is elapsed, the vacuum pump (3) is re-activated at step #7 to reduce the pressure in the interior of the reaction container (1) from P2 to P1 (second pressure reduction process S3a in FIG. 3). During the second pressure reduction process, the generation of plasma is maintained. Although the target pressure P1 in the second pressure reduction step (S3a) needs not to be exactly the same as the pressure P1 in the above-described first pressure reduction step S1, preferably they are substantially the same.

When the pressure in the interior of the reaction container (1) is reduced to P1, the high-frequency unit (4) is de-energized at step #8 to complete the generation of plasma. Then, the on-off valve (6b) in the air intake pipe (6) is opened at step #9. This causes that the atmospheric air is introduced into the reaction container (1) and then the pressure in the interior of the container (1) is reduced to the atmospheric pressure Ps. This allows that the interior of the reaction container (1) is replaced by the fresh air (see ventilation process S4 in FIG. 3).

Subsequently, the sterilized object (Jb) is removed from the reaction container (1) at step #10, which completes one cycle of sterilization process. The sterilization process may be applied to the same object several times. In this instance, steps #1 to #9 are repeated several times. If the sterilization process is carried out for another object, the steps #1 to #10 are again performed.

The above-described operation of the sterilization system (M1) may be controlled by a software program which is retrievably stored in the memory which is equipped or incorporated in the controller (EC1).

It is known that the temperature of plasma increases in proportion to pressure. The sterilization objects (Sb) including medical instruments should not be sterilized in elevated temperatures due to the material diversification of the devices. This in turn requires the temperature of plasma to be less than, for example, 60 degrees Celsius. In the plasma process S3, however, the plasma generation is initiated after the pressure has been increased to P2 (P2>P1) in the sterilization step S2, in which the temperature of the plasma tends to become relatively high before starting the second pressure reduction step (S3a). Then, before starting the second pressure reduction process (S3a), the high frequency power may be supplied intermittently or pulsatingly, rather than continuously, from the high frequency unit (4) in order to keep the temperature of the generated plasma as low as possible. In this instance, the plasma is generated intermittently or pulsatingly.

In the sterilization process according to the embodiment, the peracid agent including at least peracetic acid is used as described above. As is known well in the art, the peracetic acid ($CH_3COOOH$) usually exists in the form of an equilibrium mixture of pure peracetic acid and other components including acetic acid (CH$_3$COOH), hydrogen peroxide (H$_2$O$_2$), and water (H$_2$O) and it can be hydrolyzed into acetic acid and hydrogen peroxide as shown in the following equation (1):

$$CH_3COOOH + H_2O \rightarrow CH_3COOH + H_2O_2 \qquad (1)$$

Plasma energy, which is a special energy composed of free radical of gas molecules and ultraviolet ray, is capable of breaking the coupling between elements in molecules. By the irradiation of plasma energy, hydrogen peroxide is decomposed into water and oxygen (O$_2$) as shown in the following equation (2):

$$H_2O_2 H_2O + (1/2)O_2 \qquad (2)$$

Also, acetic acid, of which elementary coupling in molecules is broken by plasma energy, chemically reacts with oxygen generated by decomposition of hydrogen peroxide as shown by equation (2) to form carbon dioxide (CO$_2$) and water, as shown in the following equation (3):

$$2(CH_3COOH) + 4(O_2) \rightarrow 4(CO_2) + 4(H_2O) \qquad (3)$$

As described above, peracid agent including at least peracetic acid, which is used as agent in the embodiment, is eventually decomposed by the plasma energy in the plasma process (S3) after the sterilization process (S2) into odor-free stable molecules, i.e., carbon dioxide and water, by plasma energy.

According to the embodiment, the plasma is generated in the space between the external and internal boxes (1a, 1b) of the reaction container (1), which is applied primarily to the agent in the space to deodorize it to a large extent. Although no plasma is generated inside the internal box (1b), the generated plasma penetrates through the perforations of the internal box (1b) into the interior of the internal box (1b). This results in that, although it may be difficult to completely deodorize the agent remaining in the interior of the internal box (1b), the generated plasma is expected to be applied and deodorize it to some extent.

In the second pressure reduction process S3a, however, the pressure in the interior of the reaction container (1) is reduced while the plasma is generated therein. This causes the remaining agent in the internal chamber (1b) is drawn into the space between the external and internal chambers (1a, 1b) where it is exposed intensely to the plasma generated therein and thereby deodorized effectively before being exhausted out of the reaction container (1). Therefore, the gas exhausted through the exhaust pipe (3d) of the vacuum pump (3) to the exterior of the system (M1) is satisfactorily deodorized, further improving the deodorization of the reaction container (1) in the ventilation process S4, which considerably reduces strong, unpleasant and irritating odor.

As described above, according to the embodiment, in the process of reducing the pressure in the reaction container (1) after the sterilization process using peracetic agent including at least peracid agent, the plasma generation is maintained at the object receiving portion in the reaction container (1) for receiving the sterilization object (Jb) and the fluid-passage portion of the fluid passage from the neighborhood of the object receiving portion to the exterior of the system (M1), effectively deodorizing the remaining agent within the container after the sterilization process, which advantageously minimizes adverse affect on the working environment which might cause due to the irritating odor of the agent. Also, the adverse affect due to the irritating odor of the agent is reduced with a relatively simple structure in which, for example, the plasma generation portions and the pressure reduction timings are modified, without any need to install additional large and expensive deodorization equipment.

Next, other embodiments of the invention will be described below. In the following descriptions, like parts are referred to by like numerals in the first embodiment (see FIGS. 1-3) to eliminate duplicate descriptions for those parts.

Figure 4:
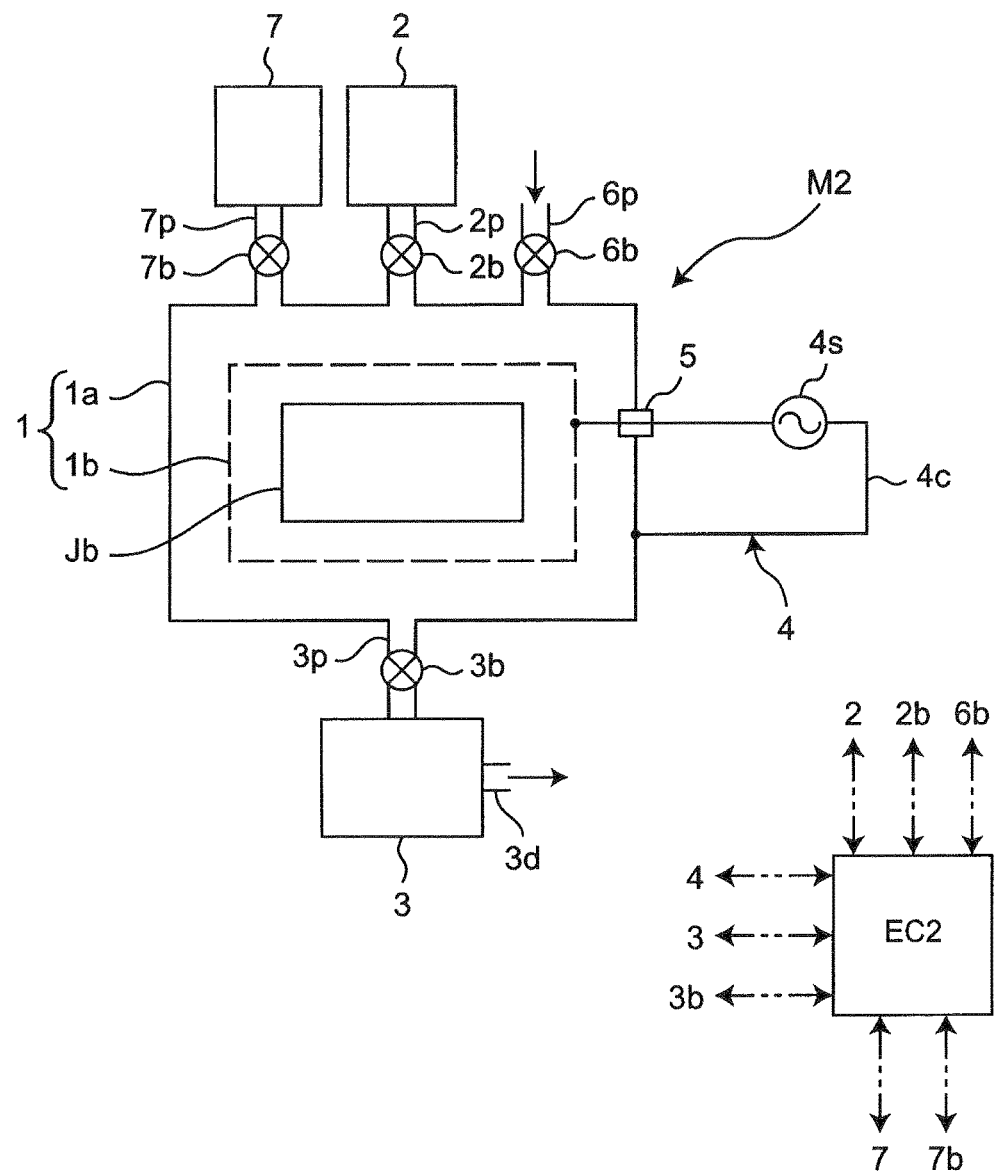
FIG. 4 is a diagram schematically showing a general construction of the sterilization system according to the second embodiment of the invention.
Figure 5:
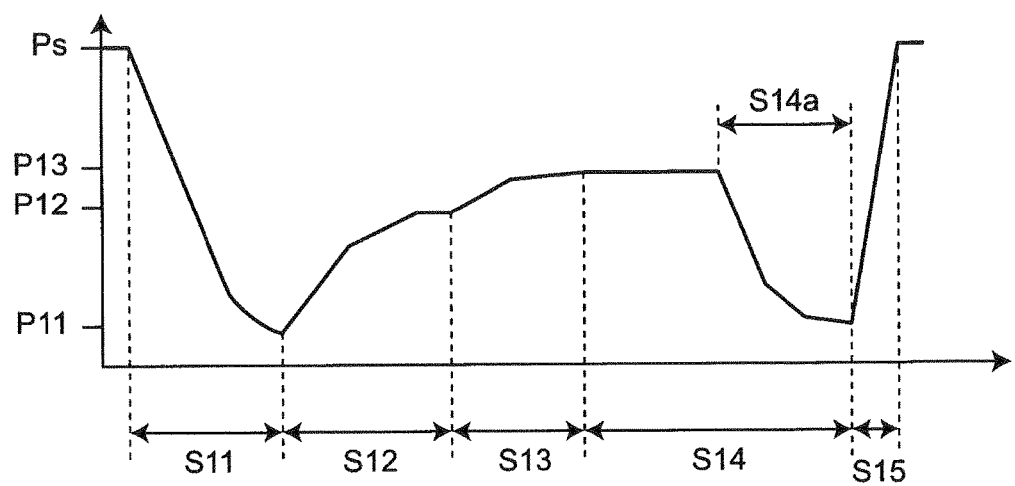
FIG. 5 is a graph showing a pressure variation in a reaction container during the process made by the sterilization system according to the second embodiment.
Figure 6:
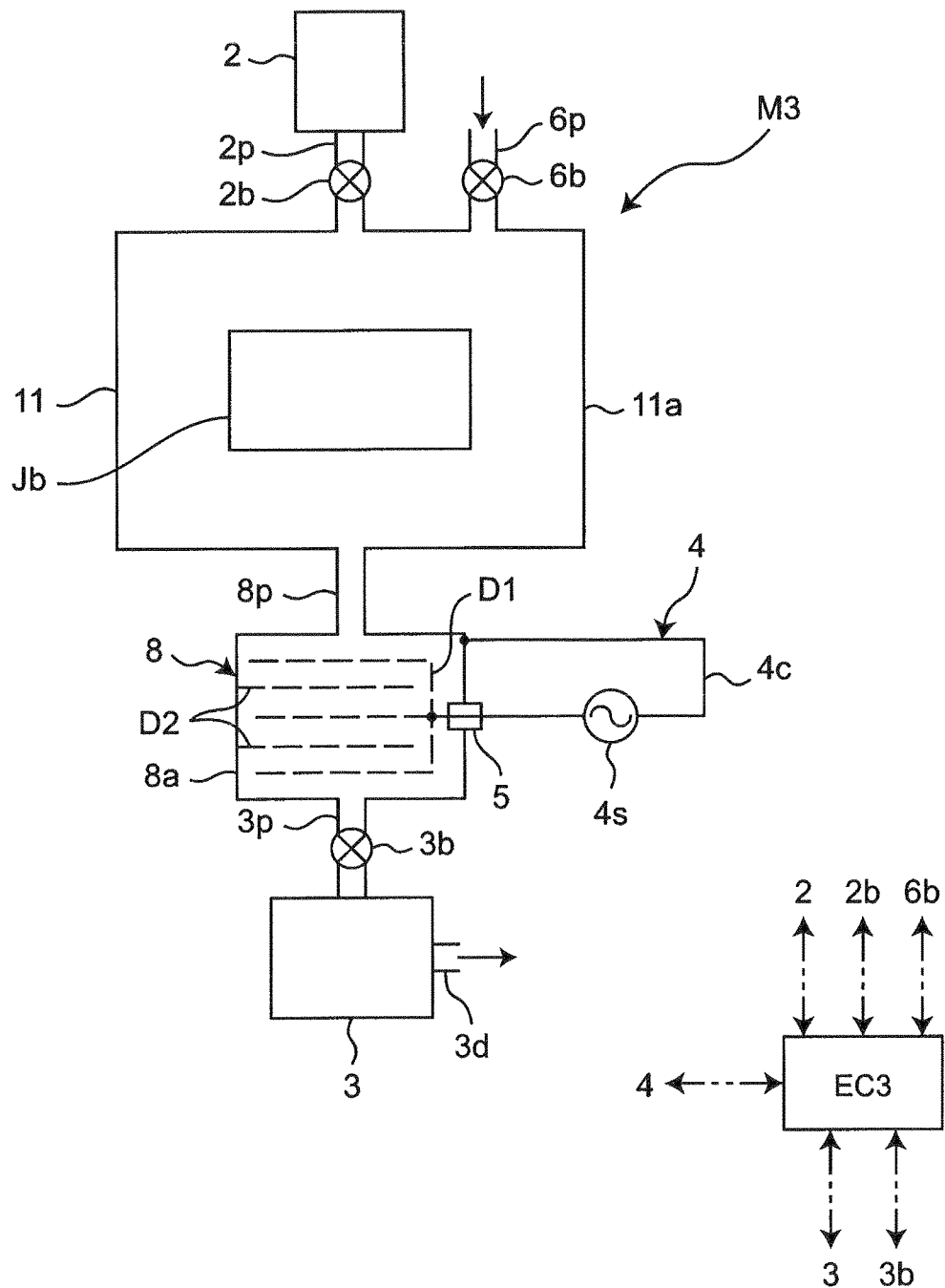
FIG. 6 is a diagram schematically showing a general construction of the sterilization system according to the third embodiment of the invention.

FIG. 4 is a diagram schematically showing a general construction of the sterilization system according to the second embodiment of the invention. FIG. 5 is a graph showing a pressure variation in a reaction container during the process made by the sterilization system (M2) according to the second embodiment. As shown in FIG. 4, in the sterilization system (M2) of this embodiment, a second agent injection unit (7) is provided beside the agent injection unit (2) and on the upstream side of the reaction container (1), which is configured to inject a decomposer which is capable of accelerating the decomposition of peracid agent or water into the reaction container (1).

The second injection unit (7) is connected to the upstream side of the reaction container (1), beside the agent injection unit (2), through an injection pipe (7p) with an on-off control valve (7b) provided therein. As can be seen by comparing FIGS. 4 and 1, the sterilization system (M2) of the second embodiment differs, from the sterilization system (M1) of the first embodiment, in that it has the second injection unit (7). Correspondingly, the controller (EC2) is connected for communication to the second injection unit (7) and the on-off control valve (7b).

According to the sterilization system (M2) of the second embodiment, as shown in FIG. 5, after the pressure in the interior of the reaction container (1) is reduced from the atmospheric pressure (Ps) to a certain pressure (P11) at the pressure reduction process S11, the agent is injected into the pressure-reduced reaction container (1) at the sterilization process S12. This results in that the vapor pressure caused by the vaporization of the agent increases the pressure in the reaction container (1) up to a certain pressure (P12) (Ps>P12>P11), during which the sterilization process is performed.

Although the processes S11 and S12 are the same as those S11 and S12 in the first embodiment, the second injection process S13 is performed after the sterilization process S12 and before the plasma process S14. In the second injection process S13, the decomposer for accelerating the decomposition of peracid agent or water is injected in the reaction container (1). by the use of the second injection unit (7). In order to accelerate the diffusion of the decomposer or water in the reaction container (1), it may be injected therein in the form of vapor. Therefore, not only the agent but also the peracid-agent decomposer or water is injected into the reaction container, which accelerates the hydrolysis of the agent (see equation (1)) and the residual agent is effectively deodorized.

The injection of the peracid-agent decomposer or water into the reaction container (1) increases the pressure in the container (1) up to a pressure P3 (Ps>P13>P12). After a predetermined time lapse from the injection of the decomposer or water into the container, similar to the first embodiment, the high frequency power source (4) is driven to perform the plasma processing (S14) in which the second pressure reduction process (S14a) begins.

When the second pressure reduction process (S14a) and the then the plasma processing (S14) are completed, the atmospheric air is introduced in the reaction container (1) in the ventilation process (S15). Then, the sterilized object (Jb) is taken out of the reaction container (1), which completes one of sterilization process. As described above, the process of the second embodiment differs from the first embodiment only in that the second injection process (S13) for injecting the decomposer or water into the reaction container (1) is performed after the sterilization step (S12) but before the plasma processing step (S14).

According to this embodiment, not only the agent but also the decomposer or water is injected into the reaction container, accelerating hydrolysis of the remaining agent, which results in an effective deodorization of the agent. The remaining agent can be hydrolyzed more effectively using peracid-agent decomposer such as catalase, than using water.

Next, a third embodiment of the invention will be described below. Although the plasma is generated only within the reaction container (1) in the previous first and second embodiments, according to the third embodiment it is generated outside the reaction container (11) of the sterilization system (M3).

Specifically, a chamber (8) for generating plasma is provided between the reaction container (11) and the vacuum pump (3). The reaction container (11) includes only an external box (11a) made of plates, preferably steel or metal plates, with certain strength, rigidity, and corrosion resistance. No internal box is needed in this embodiment because plasma is generated outside the reaction container. The plasma generation chamber (8) is connected at its upstream side to the reaction container (11) through a connection pipe (8p) and at its downstream side to the vacuum pump (3) through a connection pipe (3p).

The plasma generation chamber (8) has a casing (8a) which includes a first electrode (D1) and a second electrode (D2) mounted therein so that plasma is generated in spaces between the electrodes (D1, D2). The casing (a), the first electrode (D1), and the second electrode (D2) are made of electrically conductive material with certain strength, rigidity, and corrosion resistance. The first electrode (D1) is electrically disconnected from the casing (8a) and the second electrode (D2) is electrically connected with the casing (8a).

Preferably, the casing (8a), the first electrode (D1), and the second electrode (D2) are made of metal plate such as steel plate. Specifically, the casing (8a) is made of conventional, unperforated metal plate in order to define an interior thereinside which is air-tightly separated from its exterior. The first and second electrodes (D1, D2) are made of perforated metal plates so that fluid flows freely through perforations defined thereon.

To generate plasma, a high frequency power source (4), which is similar to the high frequency power source in the first and second embodiment, is provided beside the plasma generation chamber (8). One end of the high frequency circuit (4c) of the high frequency power source (4) is electrically connected to the casing (8a) and then the second electrode (D2). The other end of the high frequency circuit (4c) is extended through the air-tight sleeve (5) into the interior of the casing (8a) where it is electrically connected to the first electrode (D1). This allows that, by the driving of the high-frequency power source (4c), plasma is generated in the spaces between the first and second electrodes (D1, D2). The system (M3) of this embodiment further includes a controller (EC3) which is similar to that in the above-described first embodiment.

As such, according to this embodiment, the plasma is generated at the object receiving portion in the reaction container (11) for receiving the sterilization object (Jb) and the fluid-passage portion of the fluid passage from the neighborhood of the object receiving portion to the exterior of the system (M3), in which the predetermined portions are provided outside the reaction container (11), allowing the dedicated plasma generating chamber (8) for generating plasma to be provided between the reaction container (11) and the vacuum pump (3), which ensures that the plasma is effectively applied to the agent in the fluid passage. As a result, the residual agent in the reaction container (11) is effectively deodorized.

Figure 7:
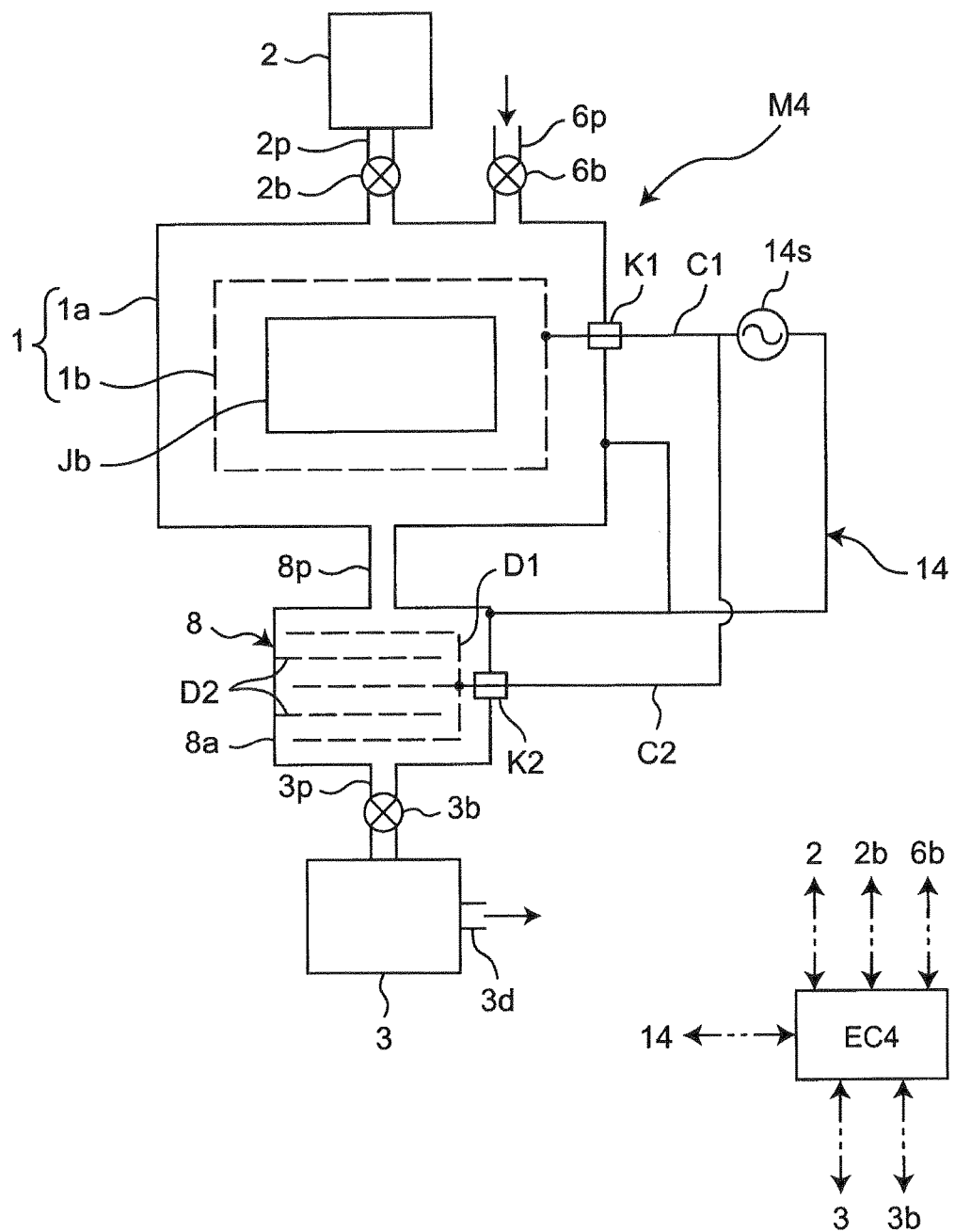
FIG. 7 is a diagram schematically showing a general construction of the sterilization system according to the fourth embodiment of the invention.

Next, a fourth embodiment of the invention will be described below. FIG. 7 is a diagram showing a schematic structure of a sterilization system (M4) according to the fourth embodiment of the invention. In the sterilization system (M49 of the fourth embodiment, the plasma generation zone is provided inside and outside the reaction container (1).

Specifically, according to the embodiment, similar to the first and second embodiments the reaction container 1 has internal and external boxes (1a, 1b) and a plasma generation chamber (8) is formed between the reaction container (1) and the vacuum pump (3) as in the third embodiment so that plasma is generated within the reaction container (1) and also within the plasma generation chamber (8) provided outside the container (1).

For this purpose, in the embodiment the high-frequency power source (14) includes first and second high-frequency circuits (C1, C2) for supplying a high-frequency power from the high frequency power source (14c) to the reaction container (1) and the plasma generation chamber (8), respectively. One end of the first high-frequency circuit (C1) is electrically connected to the external box (1a) of the reaction container (1). The other end of the circuit (C1) is extended through the air-tight sleeve (K1) and electrically connected to the internal box (1b) of the container (1). Also, one end of the second high-frequency circuit (C2) is electrically connected to the casing (8a) and then the second electrode (D2). The other end of the circuit (C2) is extended through the air-tight sleeve (K2) and electrically connected to the first electrode (D1) in the casing (8a).

This allows that, by the driving of the high-frequency power source (4s), the plasma is generated in the spaces between the external and internal boxes (1a, 1b) and, simultaneously, in the spaces between the first and second electrodes (D1, D2) within the plasma generation chamber (8). Also, the system (M4) of this embodiment includes a controller (EC4) which is similar to that in the first or third embodiment.

As described above, according to the embodiment the plasma is generated at the object receiving portion in the reaction container (1) for receiving the sterilization object (Jb) and the fluid-passage portion of the fluid passage from the neighborhood of the object receiving portion to the exterior of the system (M4), in which the predetermined portions are arranged inside and outside the reaction container (11). In particular, the outside arrangement ensures that the plasma is effectively applied to the agent in the fluid passage. Also, the inside arrangement ensures that the plasma is applied in multiple stages. As a result, the residual agent in the reaction container (1) is effectively deodorized.

In the above-described embodiments, a filter including activated carbon or alkali material such as calcium hydroxide may be provided on the downstream side of the exhaust pipe (3d) of the vacuum pump (3).

The present invention is not limited to the above-described embodiments and they may modified and/or improved in various ways without departing the spirit of the invention.

INDUSTRIAL APPLICABILITY

The present invention relates to a sterilization device and a sterilization method using the sterilization device. In particular, the present invention is effectively incorporated in a sterilization device which performs a sterilization process using, as sterilization agent, peracid agent including at least peracetic acid, and a sterilization method using the sterilization device.

PARTS LIST 1, 11: reaction container
2: agent injection unit
3: vacuum pump
4, 14: high-frequency unit
7: second injection unit
8: plasma generation chamber
Jb: sterilization object
M1, M2, M3, M4: sterilization system
EC1, EC2, EC3, EC4: controller

The invention claimed is:

1. A sterilization system, comprising:
a reaction container configured to receive a sterilization object and sterilize the sterilization object;
a first supply configured to supply a peracid agent as a sterilization agent into the reaction container to sterilize the sterilization object, the peracid agent including at least peracetic acid;
a vacuum pump configured to reduce a pressure in the reaction container;
a ventilator configured to ventilate the reaction container;
a plasma generator configured to generate plasma at a first predetermined portion for receiving the sterilization object in the reaction container and at a second predetermined portion of a fluid passage to decompose the peracid agent in the first and second predetermined portions, the fluid passage ranging from a neighborhood of the first predetermined portion to an exterior of the reaction container;
a controller configured to control the vacuum pump and the plasma generator so that the plasma is maintained at the first and second predetermined portions in a process during which the pressure in the reaction container is reduced; and
a second supply configured to supply a decomposer or water for accelerating a decomposition of the peracid agent into the reaction container after the sterilization agent has been supplied into the reaction container to accelerate decomposition of the peracid agent,
wherein the second predetermined portion is provided outside the reaction container and is a portion of the fluid passage between the reaction container and the vacuum pump.

2. A sterilization method, comprising:
receiving a sterilization object at a first predetermined portion in a sterilization reaction container;
reducing a pressure in the sterilization reaction container and supplying a peracid agent as a sterilization agent into the sterilization reaction container to sterilize the sterilization object, the peracid agent including at least peracetic acid;
after sterilizing the sterilization object, generating plasma at the first predetermined portion and at a second predetermined portion of a fluid passage from a neighborhood of the first predetermined portion to an exterior of the sterilization reaction container to decompose the peracid agent in the first and second predetermined portions;
reducing the pressure in the sterilization reaction container while maintaining the plasma at the first and second predetermined portions and then ventilating the sterilization reaction container; and
supplying a decomposer or water into the sterilization reaction container after the sterilization agent has been supplied into the sterilization reaction container to accelerate decomposition of the peracid agent.

3. A sterilization method, comprising:
receiving an object in a reaction container;
after receiving the object in the reaction container, reducing a pressure in the reaction container to a first predetermined value;
after the pressure in the reaction container reaches the first predetermined value, supplying a peracid agent as sterilization agent into the reaction container to sterilize the object, the peracid agent including at least peracetic acid;
after a completion of supplying the peracid agent into the reaction container, supplying a decomposer or water into the reaction container for accelerating a decomposition of the peracid agent;
after a completion of supplying the decomposer or water into the reaction container, generating a plasma in the reaction container to decompose the peracid agent remaining in the reaction container;
after a predetermined time elapses from a start of generating the plasma, reducing the pressure in the reaction container to a second predetermined value; and
after the pressure in the reaction container reaches the second predetermined value, ventilating the reaction container.

4. The sterilization method of claim 3, wherein the plasma is maintained in the reaction container before the pressure in the reaction container reaches the second predetermined value.

* * * * *